(12) United States Patent
Helgeson et al.

(10) Patent No.: US 10,967,150 B2
(45) Date of Patent: *Apr. 6, 2021

(54) DEFLECTABLE CATHETER SHAFT SECTION

(71) Applicant: St. Jude Medical, Cardiology Division, Inc., St. Paul, MN (US)

(72) Inventors: Zachary L. Helgeson, Richfield, MN (US); Troy T. Tegg, Elk River, MN (US); Alexander C. Houck, Hopkins, MN (US); Xuan Y. Khieu, Maple Grove, MN (US); Salome A. Gonzalez, Maple Grove, MN (US); Somally Mom, Savage, MN (US); John Her, Brooklyn Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 187 days.

This patent is subject to a terminal disclaimer.

(21) Appl. No.: 16/139,568

(22) Filed: Sep. 24, 2018

(65) Prior Publication Data

US 2019/0105469 A1 Apr. 11, 2019

Related U.S. Application Data

(63) Continuation of application No. 14/724,210, filed on May 28, 2015, now Pat. No. 10,118,022.

(60) Provisional application No. 62/008,096, filed on Jun. 5, 2014.

(51) Int. Cl.
*A61M 25/01* (2006.01)
*A61B 18/14* (2006.01)

(52) U.S. Cl.
CPC ..... *A61M 25/0147* (2013.01); *A61B 18/1492* (2013.01); *A61M 25/0141* (2013.01); *A61M 2025/015* (2013.01); *A61M 2210/12* (2013.01)

(58) Field of Classification Search
CPC .......... A61M 25/0147; A61M 25/0141; A61M 2025/015
See application file for complete search history.

(56) References Cited

U.S. PATENT DOCUMENTS

| 5,150,702 A | 9/1992 | Miyanaga et al. |
| 5,160,559 A | 11/1992 | Scovil et al. |
| 5,187,130 A | 2/1993 | Newkirk et al. |
| 5,224,803 A | 7/1993 | Lallier |

(Continued)

FOREIGN PATENT DOCUMENTS

JP H09201367 A 8/1997

*Primary Examiner* — Bradley J Osinski
(74) *Attorney, Agent, or Firm* — Dykema Gossett PLLC

(57) ABSTRACT

A deflectable catheter shaft section is disclosed comprising an elongated body extending along a longitudinal axis with a distal end and a proximal end. First and second pull wires can extend along the elongated body and can have a proximal end and a distal end. First and second pull wire liners can be disposed over a portion of one of the first and second pull wires, respectively. Each of the first and second pull wires can have a proximal end and a distal end. A first gap can exist between the proximal end of the first pull wire liner and the proximal end of the elongated body and a second gap can exist between the proximal end of the second pull wire liner and the proximal end of the elongated body.

18 Claims, 6 Drawing Sheets

(56) References Cited

U.S. PATENT DOCUMENTS

| | | |
|---|---|---|
| 5,329,923 A * | 7/1994 | Lundquist .......... A61B 18/1492 |
| | | 600/373 |
| 5,662,622 A | 9/1997 | Gore et al. |
| 7,060,050 B2 | 6/2006 | Kliem et al. |
| 7,993,481 B2 | 8/2011 | Kauphusman et al. |
| 8,187,267 B2 | 5/2012 | Pappone et al. |
| 8,814,825 B2 | 8/2014 | Tegg et al. |
| 9,044,156 B2 * | 6/2015 | Clark .................... A61B 5/042 |
| 2004/0140585 A1 | 7/2004 | Sterud et al. |
| 2007/0173757 A1 * | 7/2007 | Levine ................ A61M 25/008 |
| | | 604/95.04 |
| 2008/0004681 A1 | 1/2008 | Marshall et al. |
| 2010/0152731 A1 | 6/2010 | de la Rama et al. |
| 2010/0217234 A1 | 8/2010 | Grovender et al. |
| 2011/0125134 A1 | 5/2011 | Schwager |
| 2012/0116429 A1 | 5/2012 | Levine et al. |

\* cited by examiner

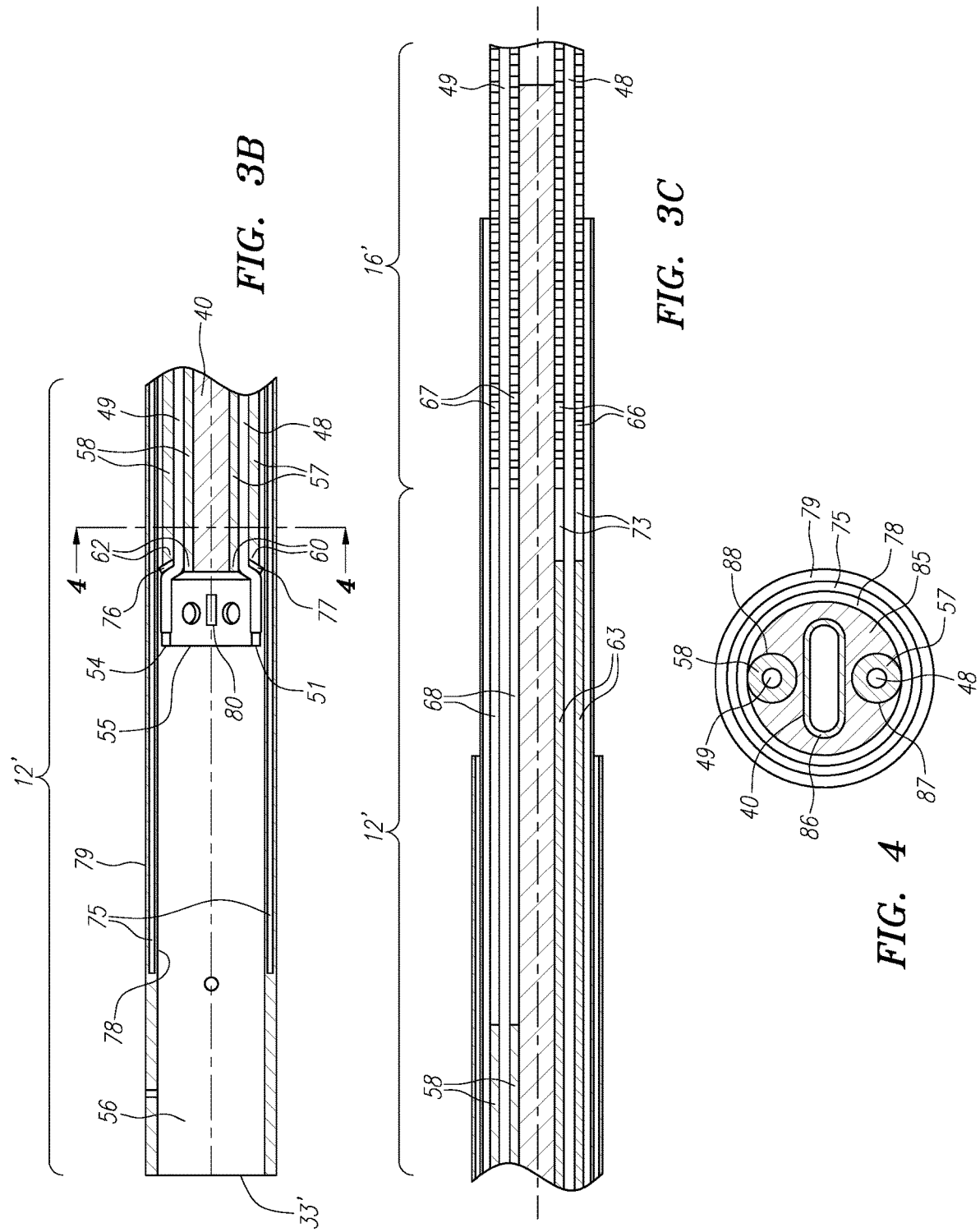

DEFLECTABLE CATHETER SHAFT SECTION

CROSS-REFERENCE TO RELATED APPLICATION

This application is a Continuation of U.S. patent application Ser. No. 14/724,210, filed 28 May 2015, now U.S. Pat. No. 10,118,022, issued 6 Nov. 2018 (the '210 application). This application claims the benefit of U.S. provisional application No. 62/008,096, filed 5 Jun. 2014 (the '096 application). The '210 application and the '096 application are both hereby incorporated by reference as though fully set forth herein.

BACKGROUND a. Field

The instant disclosure relates to a deflectable catheter shaft section and related components.

b. Background Art

Medical devices, catheters, and/or cardiovascular catheters, such as electrophysiology catheters can be used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart, which can lead to a variety of symptomatic and asymptomatic ailments and even death.

Typically, a catheter can be deployed and manipulated through a patient's vasculature to the intended site, for example, a site within a patient's heart or a chamber or vein thereof. To position a catheter within the body at a desired site, some type of navigation may be used, such as mechanical steering features incorporated into the catheter (or an introducer sheath). In some examples, medical personnel can manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pull wire attached at the distal end of the catheter that extends to a control handle that controls the application of tension on the pull wire.

The foregoing discussion is intended only to illustrate the present field and should not be taken as a disavowal of claim scope.

BRIEF SUMMARY

In various embodiments, a deflectable catheter shaft section can include an elongated body extending along a longitudinal axis that includes a distal end and a proximal end. First and second pull wires can extend along the elongated body. The first and second pull wires can each have a proximal end and a distal end. In some embodiments, first and second pull wire liners can each be disposed over a portion of one of the first and second pull wires, respectively. Each of the first and second pull wires can have a proximal end and a distal end. In some embodiments, the first and second pull wire liners can be diametrically-opposed. In some embodiments, an inner diameter of the pull wire liner can be in a range of 0.0105 inches to 0.0120 inches and an outer diameter of the pull wire liner can be in a range of 0.0140 inches to 0.0180 inches. The elongated body can include a pocket at the distal end of the elongated body configured for attachment of a pull ring and tip assembly. The distal end of each of the first and second pull wires can be connected to the pull ring. In some embodiments, a first gap can exist between the proximal end of the first pull wire liner and the proximal end of the elongated body and a second gap can exist between the proximal end of the second pull wire liner and the proximal end of the elongated body. A longitudinal length of the first gap can be greater than a longitudinal length of the second gap. In some embodiments, a bendable stiffening member can be disposed over the first pull wire along a portion of the first gap. The bendable stiffening member can have a proximal end and a distal end. The distal end of the bendable stiffening member can be spaced apart from the proximal end of the first pull wire liner and the proximal end of the bendable stiffening member can be spaced apart from the proximal end of the elongated body. In some embodiments, a longitudinal length of the first gap can be substantially the same as a longitudinal length of the second gap.

In various embodiments, a catheter can comprise an elongated body extending along a longitudinal axis, the elongated body can include a proximal catheter shaft section and a distal, deflectable catheter shaft section. First and second pull wires can extend along the proximal catheter shaft section and along the deflectable catheter shaft section. Each of the first and second pull wires can have a proximal end and a distal end and the distal end of each of the first and second pull wires can be connected to a pull ring that can be attached within a pocket at the distal end of the elongated body. In some embodiments, first and second compression coils can each be disposed over one of the first and second pull wires, respectively, along the proximal catheter shaft section. Each of the first and second compression coils can have a proximal end and a distal end. In some embodiments, first and second pull wire liners can each be disposed over a portion of one of the first and second pull wires, respectively. Each of the first and second pull wires can have a proximal end and a distal end. The first and second pull wire liners can include polytetrafluoroethylene. In some embodiments, a first gap can exist between the proximal end of the first pull wire liner and the distal end of the first compression coil and a second gap can exist between the proximal end of the second pull wire liner and the distal end of the second compression coil. A longitudinal length of the first gap can be greater than a longitudinal length of the second gap. In some embodiments, a bendable stiffening member can be disposed along a portion of the first gap. A distal gap can exist between the proximal end of the first pull wire liner and a distal end of the bendable stiffening member. A proximal gap can exist between the proximal end of the bendable stiffening member and the distal end of first compression coil. In some embodiments, the bendable stiffening member can include a spring pack disposed over the first pull wire. In some embodiments, the deflectable catheter shaft section can be configured to asymmetrically deflect along a plane defined by the first and second pull wires.

In various embodiments, a catheter can include an elongated body extending along a longitudinal axis. The elongated body can include a proximal catheter shaft section and a distal, deflectable catheter shaft section. A first and second diametrically-opposed deflection lumen can each extend longitudinally through the proximal catheter shaft section and the deflectable catheter shaft section. In some embodiments, the elongate body can include a cylindrical braid structure over the first and second diametrically-opposed lumens. First and second pull wire liners can extend through a portion of each of the deflection lumens in the deflectable shaft section. Each of the first and second pull wire liners can have a proximal end and a distal end. First and second compression coils can extend through a portion of each of the deflection lumens in the proximal shaft section. Each of the first and second compression coils can have a proximal end and a distal end. In some embodiments, a first gap can exist between the proximal end of the first pull wire liner and the distal end of the first compression coil and a second gap can exist between the proximal end of the second pull wire liner and the distal end of the second compression coil. A longitudinal length of the first gap can be substantially equal to a longitudinal length of the second gap. In some embodiments, a first pull wire can extend through the first pull wire liner, the first gap, and the first compression coil, and a second pull wire can extend through the second pull wire liner, the second gap, and the second compression coil. In some embodiments, a distal end of the first and second pull wires and the distal end of the first and second pull wire liners can be connected to a pull ring. In some embodiments, the deflectable catheter shaft section can be configured to symmetrically deflect along a plane defined by the first and second pull wires.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 3B illustrates a distal portion of the deflectable catheter shaft section seen in FIG. 3A, in accordance with embodiments of the present disclosure.

FIG. 3C illustrates a proximal portion of the deflectable catheter shaft section seen in FIG. 3A, in accordance with embodiments of the present disclosure.

FIG. 4 illustrates a cross-sectional view of the embodiment in FIG. 3B in the direction of line 4-4, in accordance with embodiments of the present disclosure.

DETAILED DESCRIPTION

Figure 1:
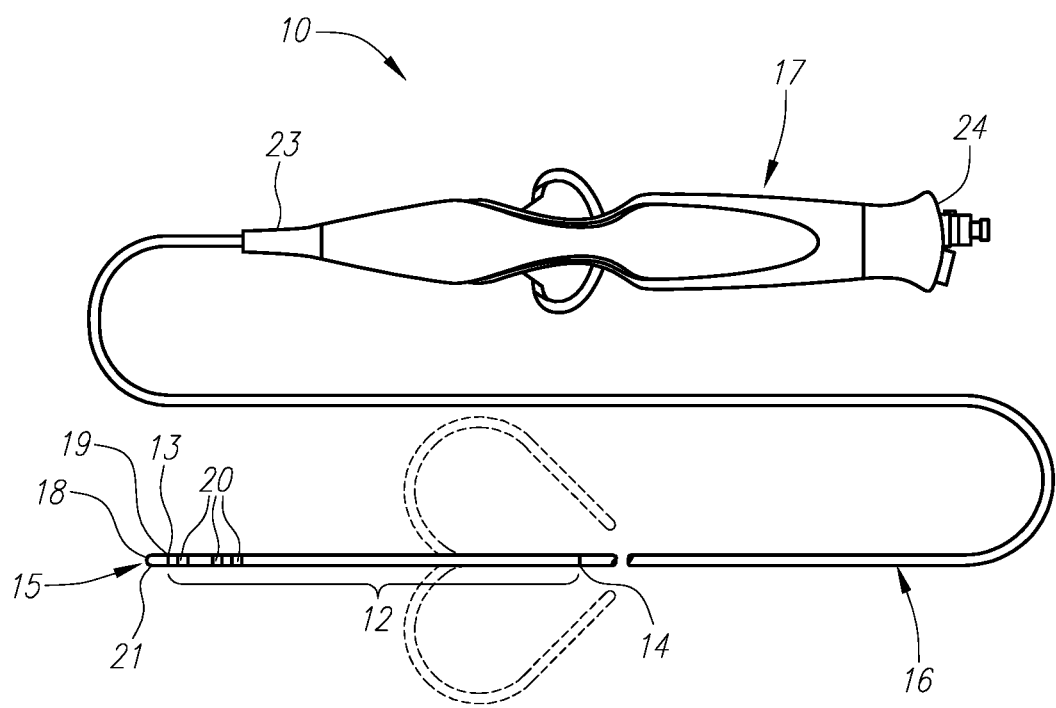
FIG. 1 illustrates a deflectable electrophysiology catheter that comprises a deflectable catheter shaft section, in accordance with embodiments of the present disclosure.

FIG. 1 illustrates a deflectable electrophysiology catheter that comprises a deflectable catheter shaft section in accordance with embodiments of the present disclosure. Deflectable catheter shaft section 12 includes an elongated body having a distal end 13 and a proximal end 14. In its most general form, catheter 10 further includes a tip assembly 15 located at the distal end 13 of the deflectable catheter shaft section 12, a proximal catheter shaft section 16 located at the proximal end 14 of the deflectable catheter shaft section 12, and a handle assembly 17. Catheter 10 may be used in any number of diagnostic and/or therapeutic applications, such as the recording of electrograms in the heart, the performance of a cardiac ablation procedure, and other similar applications/procedures. Accordingly, one of ordinary skill in the art will recognize and appreciate that the deflectable catheter shaft section and method of manufacturing the same can be used in any number of diagnostic and therapeutic applications.

The tip assembly 15 comprises a tip electrode 21 having a distal end 18 and a proximal end 19. Tip electrode 21 may be configured for various functions and may include, without limitation, an active outer surface that is configured for exposure to blood and/or tissue. The tip electrode 21 may be affixed to distal end 13 of the deflectable catheter shaft section 12 in a number of ways. For instance, the tip electrode 21 may be bonded to an inner radial surface of the deflectable catheter shaft section 12 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 21 of the tip assembly 15 may have a recess formed therein that is sufficiently sized and configured to receive a wire that is connected to the tip electrode 21, as discussed herein. One end of the wire can be connected to the tip electrode 21 and the other end can be connected to, for example, monitoring or recording or ablation devices, such as a radiofrequency (RF) generator. The wire can be a pre-coated wire that is insulated from other components in the tip assembly 15. The tip electrode 21 of the tip assembly 15 may further include a lumen formed therein that is configured to receive a thermal sensor, as discussed herein. The thermal sensor may be configured to measure the temperature of the tip electrode 21, targeted tissue, and/or the interface therebetween and provide feedback to the monitoring or recording or ablation devices described hereinabove. The tip electrode 21 may further include a fluid lumen manifold configured as a passageway for irrigation fluid.

The proximal catheter shaft section 16 can also include one or more lumens. The proximal catheter shaft section 16 can be constructed of a series of polymer layer(s) and braid structure(s). In particular, one or more wires wound to form a cylindrical braid structure can substantially surround the one or more lumens of proximal catheter shaft section 16. In addition, a polymeric material, such as polyurethane, nylon, or various types of plastic materials such as polyether block amides offered under the trademark PEBAX®, or any other suitable material, can also substantially surround the one or more lumens of proximal catheter shaft section 16. The material can have the capability to be displaced and/or to shrink when subjected to a process, such as for example, a heating process that is performed. The mechanical properties of the proximal catheter shaft section 16 can also be varied by varying the properties of the cylindrical braid structure(s) and the polymeric material (e.g., dimension of the cylindrical braid structure and/or durometers of the polymers). Additionally, the mechanical properties of the proximal catheter shaft section 16, can be varied along the length of the proximal catheter shaft section 16. Alternatively, the mechanical properties of the proximal catheter shaft section 16 can be substantially constant along the entire length of the proximal catheter shaft section 16.

The deflectable catheter shaft section 12 can be disposed between the tip assembly 15 and the proximal catheter shaft section 16 and can include a plurality of ring electrodes 20. The length and diameter of the deflectable catheter shaft section 12 can vary according to the application. Generally, the length of the deflectable catheter shaft section 12 can range from about 2 inches (18.8 mm) to about 6 inches (119.4 mm) and the diameter of the deflectable catheter shaft section 12 can range from about 5 French to about 12 French. The diameter of the deflectable catheter shaft section 12 can be about 7 French in accordance with some embodiments. Although these particular dimensions are mentioned in particular, the dimensions of the deflectable catheter shaft section 12 can vary in accordance with various applications of the deflectable catheter shaft section 12.

The deflectable catheter shaft section 12 can be configured for deflection independent of the proximal catheter shaft section 16. The deflectable catheter shaft section 12 can be constructed of a series of polymer layer(s) and braid structure(s), which can be different than those used in the proximal catheter shaft section 16. In particular, one or more wires wound to form a cylindrical braid structure can substantially surround the one or more lumens of deflectable catheter shaft section 12. In addition, a polymeric material, such as polyurethane, nylon, or various types of plastic materials such as polyether block amides offered under the trademark PEBAX®, or any other suitable material, can also substantially surround the one or more lumens of deflectable catheter shaft section 12. The material can have the capability to be displaced and/or to shrink when subjected to a process, such as for example, a heating process that is performed. The mechanical properties of the deflectable catheter shaft section 12 can also be varied independent of the proximal catheter shaft section 16 by varying the properties of the cylindrical braid structure(s) and the polymeric material (e.g., dimension of the cylindrical braid structure and/or durometers of the polymers). Additionally, the mechanical properties of the deflectable catheter shaft section 12, can be varied along the length of the deflectable catheter shaft section 12. Alternatively, the mechanical properties of the deflectable catheter shaft section 12 can be substantially constant along the entire length of the deflectable catheter shaft section 12.

The handle assembly 17 can be coupled to the proximal catheter shaft section 16 at its proximal end (disposed within handle assembly 17 and not shown). The handle assembly 17 can be operative to, among other things, effect movement (i.e., deflection) of the deflectable catheter shaft section 12. The handle assembly 17 includes a distal end 23 and a proximal end 24. The handle assembly 17 includes an actuator that can be selectively manipulated to cause deflectable catheter shaft section 12 to deflect in one or more directions (e.g., up, down, left, and right). Deflectable catheter shaft section 12 may be configured for symmetric deflection in accordance with some embodiments and may be configured for asymmetric deflection in accordance with other embodiments, as discussed herein.

The catheter 10 may include any number of other elements such as, for example and without limitation, thermocouples, thermistor temperature sensors, etc. for monitoring the temperature of targeted tissue and controlling the temperature. In some embodiments, the catheter 10 can include a sensor for producing signals indicative of catheter location information, and may include one or more electrodes. In an example, the catheter 10 may include ring electrodes 20 that collectively define the sensor. The one or more electrodes may be provided on a distal end 13 of the catheter 10 and a localization system (e.g., EnSite™ Velocity™ system) may compute a distal location of the catheter 10 using received location information from the one or more electrodes and/or a geometrical relationship between the one or more electrodes.

In various embodiments, the catheter 10 can include a flexible tip assembly, which can include, for example, a flexible tip electrode from a Therapy™ Cool Flex™ ablation catheter manufactured by St. Jude Medical, Inc. of St. Paul, Minn. Additional details regarding a flexible electrode tip may be found in, for example, U.S. Pat. No. 8,187,267 B2 and United States patent application publication no. US 2010/0152731 A1, each of which is hereby incorporated by reference as though fully set forth herein.

Figure 2:
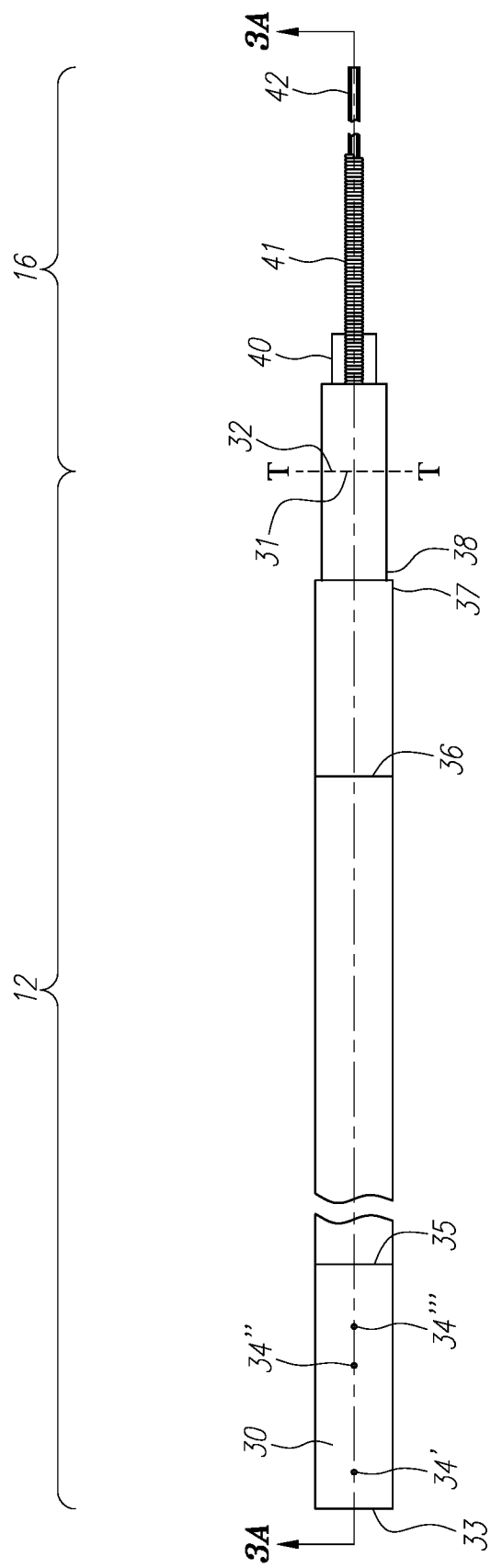
FIG. 2 illustrates a deflectable electrophysiology catheter that comprises a proximal catheter shaft section and a distal, deflectable catheter shaft section in accordance with embodiments of the present disclosure.

FIG. 2 illustrates a deflectable electrophysiology catheter that comprises a proximal catheter shaft section and a distal, deflectable catheter shaft section in accordance with embodiments of the present disclosure. The transition between the proximal catheter shaft section 16 and the deflectable catheter shaft section 16 can be defined by the transition line T-T. The deflectable catheter shaft section 12 can include an elongated body that extends along a longitudinal axis and can include a proximal end 31 and a distal end 33. The proximal catheter shaft section 16 can be an elongated body that extends along the longitudinal axis and can include a proximal end (not shown) and a distal end 32. As discussed herein, the mechanical properties of the deflectable catheter shaft section 12 can be different from the mechanical properties of the proximal catheter shaft section 16. This can provide the deflectable catheter shaft section 12 with a different deflection than the proximal catheter shaft section 16, which can be beneficial when steering the catheter through a tortuous vasculature and/or accessing a particular area of the heart, in an example.

As discussed herein, the deflectable catheter shaft section 12 and the proximal catheter shaft section 16 can be constructed of a series of polymer layer(s) and cylindrical braid structure(s). The mechanical properties of the deflectable catheter shaft section 12 can be varied by varying the properties of the polymeric material (e.g., dimension of the cylindrical braid structure and/or durometers of the polymers) and the cylindrical braid structure(s) that form the deflectable catheter shaft section 12. Additionally, the mechanical properties of the deflectable catheter shaft section 12 can be varied along the length of the deflectable catheter shaft section 12 in accordance with some embodiments of the present disclosure or can be substantially constant along the entire length of the deflectable catheter shaft section 12 in accordance with other embodiments of the present disclosure.

The deflectable catheter shaft section 12 can include a pocket 30 that can include a recessed area in the distal end 33 of the deflectable catheter shaft section 12 configured for attachment of a pull ring assembly and/or a tip assembly 15.

Holes 34', 34", 34''' can be formed through a side-wall of pocket 30 so an adhesive can be introduced into the pocket 30 for securing the pull ring assembly, tip assembly 15, and/or other various components associated with the catheter 10. The deflectable catheter shaft section 12 can include transitional segments 35, 36, where mechanical properties of the deflectable catheter shaft section 12 can change. For instance, as discussed herein, the section located between transition 35 and transition 36 can have different mechanical properties than the section located proximally from transition 36 and/or the section located distally from transition 35.

In some embodiments, the catheter 10 can include a lumen 38, as further illustrated in relation to FIG. 4. In an example, the lumen 38 can contain three lumens, although examples are not so limited, and the lumen 38 can contain more than three lumens or fewer than three lumens. For example, the lumen 38 can include four lumens. In some embodiments, a layer 37 (e.g., polymer layer) can be formed over the lumen 38 via a reflow process, in an example. The layer 37 can be formed over the lumen 38 to adjust mechanical properties of the deflectable catheter shaft section 12. The lumen 38 can have multiple lumens (e.g., four lumens) through which various componentry of the catheter 10 can be inserted. In some embodiments, lumen 40 can extend through the lumen 38. For instance, a lumen 40 can extend through the lumen 38 and provide a lubricious surface, insulation of components within lumens of the lumen 38, etc. In an example, the lumen 40 can be configured for housing wiring for electrodes or for other electrical components and/or the lumen 40 can be configured for use as an irrigation fluid passageway.

In some embodiments, the proximal catheter shaft section 16 can include a number of compression coils 41 that can pass through a portion of the lumen 38. In some embodiments, the number of compression coils 41 can be tightly wound and disposed in the proximal catheter shaft section 16. In an example, the number of compression coils 41 can each include a proximal and distal end. The distal end of the number of compression coils 41 can extend to an interface or proximate to the interface between the proximal end 31 of the deflectable catheter shaft section 12 and the distal end 32 of the proximal catheter shaft section 16. The number of compression coils 41 can be formed of stainless steel, in some embodiments, and can be disposed over a number of pull wires 42. The number of pull wires 42 can each include a distal end, which can be attached to the pull ring, and a proximal end, which can be attached to the handle assembly 17. The number of pull wires 42 can extend from the pull ring (shown in FIG. 3A), through the deflectable catheter shaft section 12, through the proximal catheter shaft section 16 to the handle assembly 17. The number of compression coils 41 can extend the entire length of the proximal catheter shaft section 16 in accordance with some embodiments of the present disclosure. In some embodiments, one or more lumens of the proximal catheter shaft section 16 can be lined with liners (not shown) that serve the purpose of providing a lubricious surface (e.g., to allow for the sliding of the number of pull wires 42). If provided, the liners may be constructed of a polymeric material, such as PTFE, or any other suitable material.

Figure 3A:
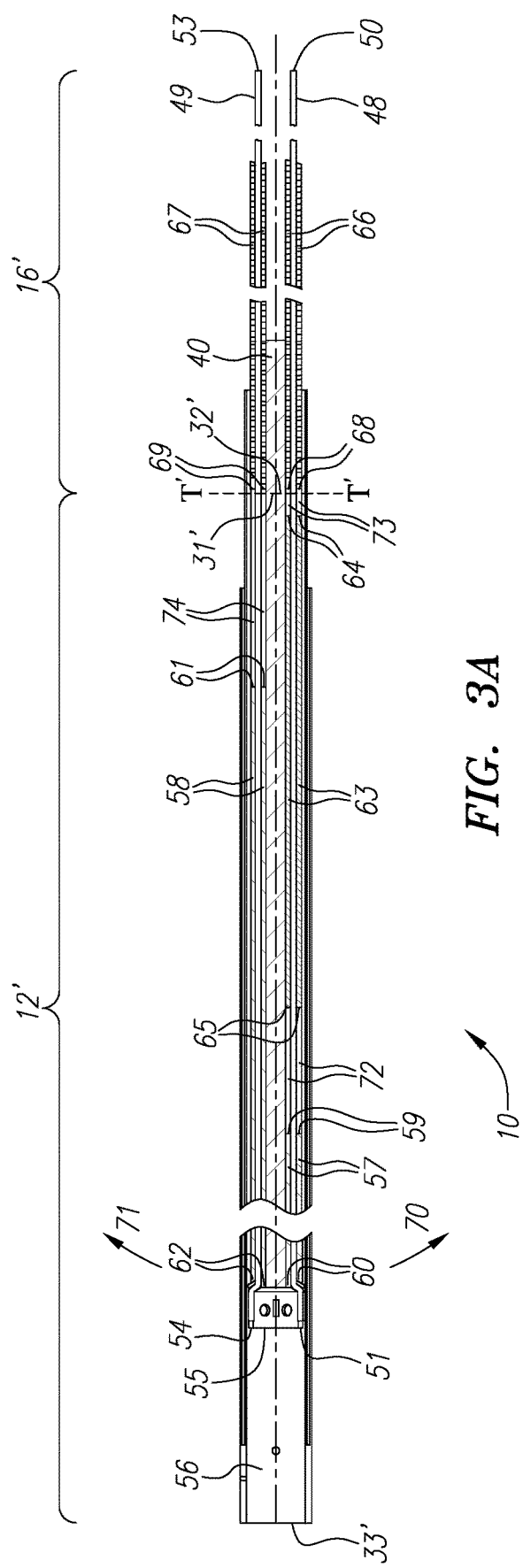
FIG. 3A illustrates a cross-sectional view of the embodiment seen in FIG. 2 taken along line 3A-3A, in accordance with embodiments of the present disclosure.

FIG. 3A illustrates a cross-sectional view of the embodiment seen in FIG. 2 taken along line 3A-3A, in accordance with embodiments of the present disclosure. A catheter 10 can include an elongate body that extends along a longitudinal axis that has a distal, deflectable catheter shaft section 12' and a proximal catheter shaft section 16'. The deflectable catheter shaft section 12' can extend along the longitudinal axis and can include a proximal end 31' and a distal end 33'. The proximal catheter shaft section 16' can extend along the longitudinal axis and can include a proximal end (not shown) and a distal end 32'. As discussed herein, mechanical properties of the deflectable catheter shaft section 12' can be different from the mechanical properties of the proximal catheter shaft section 16'. In some embodiments, the proximal end 31' of the deflectable catheter shaft section 12' can be approximately defined by transition line T'-T', for example, proximate to a distal ends 68, 69 of the compression coils 66, 67. In some embodiments, the distal end 32' of the proximal catheter shaft section 16' can be defined by the transition line T'-T', for example, proximate to the distal ends 68, 69, of the compression coils 66, 67.

The deflectable catheter shaft section 12' can include a first pull wire 48 and a second pull wire 49. Although the catheter 10 is described and illustrated as including two opposing pull wires 48, 49, it should be noted that the catheter 10 is not limited to two opposing pull wires 48, 49. Rather, the catheter 10 may include a single pull wire arrangement in some embodiments of the present disclosure. The catheter 10 may include more than two pull wires in other embodiments of the present disclosure. The pull wires 48, 49 may be formed from a superelastic Nitinol wire, carbon fiber, para-aramid synthetic fiber generally available from DuPont under the brand name KEVLAR®, or other suitable material in accordance with various embodiments of the present disclosure.

The first pull wire 48 can have a proximal end 50 and a distal end 51 and the second pull wire 49 can have a proximal end 53 and a distal end 54. The first pull wire 48 and the second pull wire 49 can extend along the deflectable catheter shaft section 12' and the proximal catheter shaft section 16'. The proximal ends 53, 50 of the pull wires 48, 49 can be attached to the handle assembly 17 and the distal ends 51, 54 can be attached to a pull ring 55 attached in a pocket 56 located at the distal end 33' of the deflectable catheter shaft section 12', which can also be configured to accept tip assembly 15. Pull wires 48, 49 can be attached to diametrically opposite locations on the pull ring 55 by a solder or weld joint, for example. The pull wires 48, 49 can extend from the pull ring 55 toward the handle assembly 17. Pulling of the pull wires 48, 49 via the handle assembly 17 can cause the pull ring 55 to tilt or rock, thereby deflecting the deflectable catheter shaft section 12'.

In some embodiments, the catheter 10 can include a first pull wire liner 57 and a second pull wire liner 58, which can be disposed over the first and second pull wires 48, 49, respectively, along a portion of the deflectable catheter shaft section 12'. The first pull wire liner 57 can have a proximal end 59 and a distal end 60 and the second pull wire liner 58 can have a proximal end 61 and a distal end 62. The distal ends 60, 62 of the pull wire liners 57, 58 can be attached to diametrically opposite locations on the pull ring 55 via an adhesive, in an example. The pull wire liners 57, 58 can be inserted into deflection lumens, as illustrated in FIG. 4. In an example, the compression coils 66, 67 and/or the bendable stiffening member 63 can be installed in the catheter 10 first and then the pull wire liners 57, 58 can be installed in the catheter 10 next.

In some embodiments of the present disclosure, the pull wire liners 57, 58 can be formed of a polytetrafluoroethylene. Forming the pull wire liners 57, 58 of polytetrafluoroethylene, can allow for an increased lubricity, an increased durability, and an increased strength associated with the pull wire liners. In an example, the increased lubricity can decrease frictional forces that can exist between the pull wire liner and the pull wire. Decreased frictional forces can be beneficial as the deflectable catheter shaft section 12' is deflected. For example, as the deflectable catheter shaft section 12' is deflected, the pull wires 48, 49 move within the pull wire liners 57, 58 and slide against an inner wall of the pull wire liners 57, 58. Increasing the lubricity of the pull wire liners 57, 58 can allow the pull wires 48, 49 to slide more easily and be subjected to less of a frictional force generated by the contact between the pull wires 48, 49 and the inner wall of the pull wire liners 57, 58. Decreased frictional force between the pull wires 48, 49 and the pull wire liners 57, 58 can reduce a deflection force associated with the catheter 10. The deflection force can be defined as a requisite force that is applied to the pull wires 48, 49 in order to cause the deflectable catheter shaft section 12' to deflect. For example, prior methods that use a pull wire liner material that is less lubricious than polytetrafluoroethylene and/or do not use pull wire liners, can be associated with a greater deflection force, as a result of the increased friction between the pull wire and a wall of a lumen that houses the pull wire.

In addition, the lubricity of the polytetrafluoroethylene pull wire liners 57, 58 improves a curve angle functionality associated with the deflectable catheter shaft section 12'. The curve angle functionality can be defined as a degree of curvature formed by the deflectable catheter shaft section 12'. For instance, when increased frictional forces are present between the pull wires and a housing that holds the pull wires, tension applied to the pull wires via the handle assembly may be lost due to frictional forces present between the pull wires and their respective housings. As such, a reduced amount of tension can be applied to the pull ring, resulting in the pull ring rocking or tilting less and thus a smaller curve angle of the deflectable catheter shaft section. Accordingly, use of polytetrafluoroethylene pull wire liners 57, 58 in embodiments of the present disclosure can cause an increased amount of tension to be applied to the pull ring 55 via the handle assembly 17, resulting in the pull ring 55 rocking or tilting more and thus a greater curve angle of the deflectable catheter shaft section 12'.

The lubricity of the polytetrafluoroethylene pull wire liners 57, 58 can also provide an increased return to straight functionality. The return to straight functionality can be defined as a propensity of the deflectable catheter shaft section 12' to return to a straight position (e.g. position along the longitudinal axis) after being placed in a deflected position when an equal amount of tension is applied to each pull wire 48, 49 via the handle assembly 17. In an example, as discussed herein, frictional forces between pull wires and their respective housings can reduce an amount of tension applied to the pull ring. Embodiments of the present disclosure can reduce the frictional forces between the pull wires 48, 49 and the pull wire liners 57, 58 through use of the polytetrafluoroethylene pull wire liners 57, 58. Accordingly, embodiments of the present disclosure can result in a reduction of deflection force associated with the catheter 10, an improved curve angle functionality, and an increased return to straight functionality.

Some embodiments of the present disclosure can provide an increased durability and strength associated with the pull wire liners 57, 58, as discussed herein. In an example, the polytetrafluoroethylene pull wire liners 57, 58 can be less susceptible to wear and/or damage from the pull wires 48, 49. In an example, some prior methods that use a pull wire liner material other than polytetrafluoroethylene and/or do not use pull wire liners can be susceptible to the pull wire cutting into a wall of a respective housing and/or cutting through the deflectable catheter shaft section, thus causing the pull wire to protrude from an exterior of the deflectable catheter shaft section, as it is deflected. Accordingly, use of polytetrafluoroethylene in embodiments of the present disclosure can provide cut and wear resistant pull wire liners 57, 58, thus increasing a durability and strength associated with the pull wire liners 57, 58 and reducing wear to the pull wire liners 57, 58, caused by the pull wires 48, 49.

In some embodiments, the pull wire liners 57, 58 of the present disclosure can be sized to improve an alignment of the pull wires 48, 49 inside of the pull wire liners 57, 58. In an example, it can be preferred that the deflectable catheter shaft section 12 bends along a plane that bisects a center of the pull wire liners 57, 58 and/or pull wires 48, 49. In some prior methods, a pull wire liner can have an increased wall thickness to provide an increased strength and durability of the pull wire liner. In an example, prior methods can have a pull wire liner that has an inner diameter of 0.010 inches and an outside diameter of 0.019 inches. However, the increased wall thickness can cause the pull wire liner to be less flexible and to resist bending. Because of the increase wall thickness of the pull wire liners used in prior methods, the pull wire liners of prior methods can resist being curved in the plane and can thus cause the deflectable catheter shaft section to form a curve that is not planar. In an example, as the deflectable catheter shaft section curves in a non-planar orientation, the pull wire liners can shift within the pull wire liners, which can exacerbate the non-planar curve. As discussed herein, it can be preferred that the deflectable catheter shaft section 12 bends along a plane that bisects a center of the pull wire liners 57, 58 and/or pull wires 48, 49. As such, when a curve is introduced into the deflectable catheter shaft section 12 via the pull wires 48, 49 and the pull ring 55, the curve can be formed along the plane.

Accordingly, in embodiments of the present disclosure, the pull wire liners 57, 58 can be formed with a wall thickness that is thinner than pull wire liners of prior methods. The pull wire liners 57, 58 of the present disclosure can have an inner diameter in a range of 0.0105 to 0.0120 inches and an outer diameter in a range of 0.0140 to 0.0180 inches. Generally, the smaller wall thickness of the pull wire liners 57, 58 employed in the present disclosure are possible because of the increased strength and durability associated with polytetrafluoroethylene. As such, pull wire liners 57, 58 can be more flexible and less resistant to bending than those employed by prior methods. Accordingly, as the pull wire liners 57, 58 are curved, the pull wire liners 57, 58 can be more likely to form a planar curve and thus improve an alignment of the pull wires 48, 49.

In some embodiments, a bendable stiffening member 63 (e.g., a 'coil pack' or a 'spring pack' or an 'uncompacted spring pack' or a 'deflection facilitator') can be disposed over the first pull wire 48 between a proximal end 59 of the first pull wire lumen 57 and a proximal end 31' of the deflectable catheter shaft section 12'. In some embodiments, the bendable stiffening member 63 can include a proximal end 64 and a distal end 65. In an example, the proximal end 64 of the bendable stiffening member 63 can be spaced apart from the proximal end 31' of the deflectable catheter shaft section 12'. In some embodiments, a first compression coil 66 can be disposed over the first pull wire 48 along the proximal catheter shaft section 16'. The bendable stiffening member 63 can be spaced apart from a distal end 68 of the first compression coil 66. In addition, the distal end 65 of the bendable stiffening member 63 can be spaced apart from the proximal end 59 of the first pull wire liner 57. A distal gap 72 can exist between the proximal end 59 of the first pull wire liner 57 and a distal end 65 of the bendable stiffening member 63.

In addition, a proximal gap 73 can exist between the proximal end 64 of the bendable stiffening member 63 and the distal end 68 of the first compression coil 66. In an example, the gaps can be annular lumens of empty space that surround the first pull wire 48 between the proximal end 59 of the first pull wire liner 57 and the distal end 65 of the bendable stiffening member 63 and between the proximal end 64 of the bendable stiffening member 63 and the distal end 68 of the first compression coil 66. In some embodiments, the bendable stiffening member 63 may not be included between the proximal end 59 of the first pull wire liner 57 and the distal end 68 of the first compression coil 66. As such, a first gap can exist between the proximal end 59 of the first pull wire liner 57 and the distal end 68 of the first compression coil 66.

In some embodiments, a second gap 74 can exist between the proximal end 61 of the second pull wire liner 58 and a proximal end 31' of the deflectable catheter shaft section 12'. In some embodiments, a second compression coil 67 can be disposed over the second pull wire 49 along the proximal catheter shaft section 16'. The second gap 74 can be an annular lumen that surrounds the second pull wire 49 between the proximal end 61 of the second pull wire liner 58 and the distal end 69 of the second compression coil 67.

In some embodiments, the second pull wire liner 58 can extend further proximally along the deflectable catheter shaft section 12' than the first pull wire liner 57. As such, in embodiments where the bendable stiffening member 63 is not included in the catheter 10, a first gap can exist between the proximal end 59 of the first pull wire liner 57 and the proximal end 31' of the deflectable catheter shaft section 12' (distal end 68 of the first compression coil 66). Accordingly, the first gap existing along the first pull wire 48 can have a longitudinal length that is greater than a longitudinal length of the second gap 74 existing along the second pull wire 49.

In some embodiments, the deflectable catheter shaft section 12' can be configured to asymmetrically deflect along a plane defined by the first and second pull wires 48, 49 and/or pull wire liners 57, 58. In an example, it can be preferred that the deflectable catheter shaft section 12' bends along a plane that bisects a center of the pull wire liners 57, 58 and/or pull wires 48, 49, as discussed herein. In addition, it can be preferred that the deflectable catheter shaft section 12' form different curves as it is deflected in the direction of arrow 70 versus when it is deflected in the direction of arrow 71. As such, the deflectable catheter shaft section 12' can be configured to asymmetrically deflect along the plane defined by the pull wire liners 57, 58 and/or pull wires 48, 49, as discussed herein. For instance, as a result of the pull wire liners 57, 58 being different lengths, and inclusion of the bendable stiffening member 63 between the proximal end 59 of the first pull wire liner 57, the deflectable catheter shaft section 12' can have a propensity to form a greater curve angle in the direction of arrow 71 than in the direction of arrow 70. Alternatively, if the bendable stiffening member 63 is not disposed around the first pull wire 48, the deflectable catheter shaft section 12' may be inclined to have a greater curve angle in the direction of arrow 70 than in the direction of arrow 71.

In some prior methods that include a pull wire liner disposed around a pull wire, an end of the pull wire liner can abut a compression coil and/or another component that is also disposed around the pull wire. As such, little to no space may exist between the pull wire liner and the compression coil. When the deflectable section that includes the pull wire liner bends, the pull wire liner can inelastically compress against the compression coil and/or other component that abuts the pull wire liner, causing an interference between the pull wire liner and the compression coil and/or other component. Because the pull wire liner is inelastic, the pull wire liner will not compress and/or compresses minimally when it contacts the compression coil and/or other component. Therefore, the interference between the pull wire liner and compression coil and/or other components can cause the deflectable section of the catheter to resist bending, which can increase a deflection force and decreases a curve angle of the deflectable section.

Accordingly, embodiments of the present disclosure can include the distal gap 72 between the first pull wire liner 57 and the bendable stiffening member 63 and the proximal gap 73 between the bendable stiffening member 63 and the first compression coil 66. In addition, embodiments of the present disclosure can include the second gap 74 between the second pull wire liner 58 and the second compression coil 67. In embodiments that do not include the bendable stiffening member 63, the first gap can be provided between the proximal end 59 of the first pull wire liner 57 and the distal end 68 of the first compression coil 66. As such, as the deflectable catheter shaft section 12' is deflected, the pull wire liners 57, 58 have space to move within the gaps. This can provide a decreased deflection force and an increased curve angle associated with the deflectable catheter shaft section 12'. In an example, the bendable stiffening member 63 can be disposed along a portion of the first gap, when the bendable stiffening member 63 is included.

In some embodiments, a size of the gaps can be varied for given curve shapes of the deflectable catheter shaft section 12'. For example, a cut length of the pull wire liners 57, 58 can be varied to cause the deflectable catheter shaft section 12' to have a greater curve angle when deflected in a direction of arrow 70 versus when the deflectable catheter shaft section 12' is deflected in a direction of arrow 71. In an example, the curve angle of the deflectable catheter shaft section 12' can be increased as the cut length of one or both of the pull wire liners 57, 58 is decreased. Alternatively, the curve angle of the deflectable catheter shaft section 12' can be decreased as the cut length of one or both of the pull wire liners 57, 58 is increased.

FIG. 3B illustrates a distal portion of the deflectable catheter shaft section seen in FIG. 3A, in accordance with embodiments of the present disclosure. The deflectable catheter shaft section 12' includes a distal end 33'. In some embodiments, the catheter 10 can include a cylindrical braid structure(s) 75 placed around pull wire liners 57, 58 and lumen 40. Deflectable catheter shaft section 12' can be constructed of a series of polymer layer(s) (e.g., inner polymer layer 78 and outer polymer layer 79) and braid structure(s) 75. In particular, one or more wires wound to form the cylindrical braid structure(s) 75 can substantially surround the pull wire liners 57, 58 and lumen 40. In addition, a polymeric material, such as polyurethane, nylon, or various types of plastic materials such as polyether block amides offered under the trademark PEBAX®, which is a registered trademark of Arkema France, Puteaux, France, or any other suitable material, can also substantially surround the pull wire liners 57, 58 and lumen 40. The material can have the capability to be displaced or to shrink when subjected to a process, such as for example, a heating process that is performed. In an example, assembly can include sliding the cylindrical braid structure(s) 75 over the inner polymer layer 78 and then sliding the outer polymer layer 79 over the cylindrical braid structure(s) 75 and applying heat to reflow the polymer layers.

The deflectable catheter shaft section 12' can include a pocket 56 that is configured to house a pull ring 55. The pull ring 55 can be attached within the pocket 56 via an adhesive 80, in some embodiments. The pull wire liners 57, 58 can be disposed over the pull wires 48, 49. A distal end 60, 62 of the pull wire liners 57, 58 can be attached to the pull ring 55 via an adhesive 76, 77. In addition, a distal end 51, 54 of the pull wires 48, 49 can be attached to the pull ring 55 via an adhesive.

FIG. 3C illustrates a proximal portion of the deflectable catheter shaft section and a proximal portion of the catheter shaft seen in FIG. 3A, in accordance with embodiments of the present disclosure. The proximal portion of the deflectable catheter shaft section 12' can include the proximal gap 73 between the bendable stiffening member 63 and first compression coil 66 and the distal gap (not shown) between the first pull wire liner (not shown) and the bendable stiffening member 63. The proximal portion of the deflectable catheter shaft section 12' can also include the second gap 74 between the second pull wire liner 58 and the second compression coil 67. The first pull wire 48 can pass through the first compression coil 66, the proximal gap 73, the bendable stiffening member 63, the distal gap 72, and the first pull wire liner 57. The second pull wire 49 can pass through the second compression coil 67, the second gap 74, and the second pull wire liner 58. As discussed herein, the gaps between the first pull wire liner 57 and the bendable stiffening member 63 and the gap between the second pull wire liner 58 and the second compression coil 67 can provide the pull wire liners 57, 58 space to move within the gaps, as the deflectable catheter shaft section 12' is deflected. This can provide a decreased deflection force and an increased curve angle associated with the deflectable catheter shaft section 12'.

FIG. 4 illustrates a cross-sectional view of the embodiment in FIG. 3B in the direction of line 4-4, in accordance with embodiments of the present disclosure. In an example, the cross-sectional view can include an outer polymer layer 79, a braid layer (braid structure(s) 75), inner polymer layer 78. For purposes of clarity, cross-hatching has been omitted from layers 75, 78, 79. In some embodiments, a lumen 85 can contain three lumens. Although the deflectable catheter shaft section 12' is described and illustrated as including three lumens, it should be noted that the deflectable catheter shaft section 12' of catheter 10 is not limited to three lumens. Rather, the deflectable catheter shaft section 12' of catheter 10 may include fewer than three lumens or more than three lumens. In an example, a first pull wire liner 57 can be diametrically opposed to a second pull wire liner 58. The pull wire liners 57, 58 can be disposed in a first deflection lumen 87 and a second deflection lumen 88. The first pull wire liner 57 can be disposed over a first pull wire 48 and the second pull wire liner 58 can be disposed over a second pull wire 49. The lumen 85 can include a lumen 40, which can be configured for housing wiring for electrodes or for other electrical components and/or for use as an irrigation fluid passageway. In an example, a lumen liner 86 can pass through the lumen 40, although examples are not so limited. In some examples, as discussed herein, the lumen 85 can include four lumens, two of which can be deflection lumens and two of which can be used for housing wiring for electrodes and/or for use as an irrigation fluid passageway, although examples are not so limited.

Figure 5A:
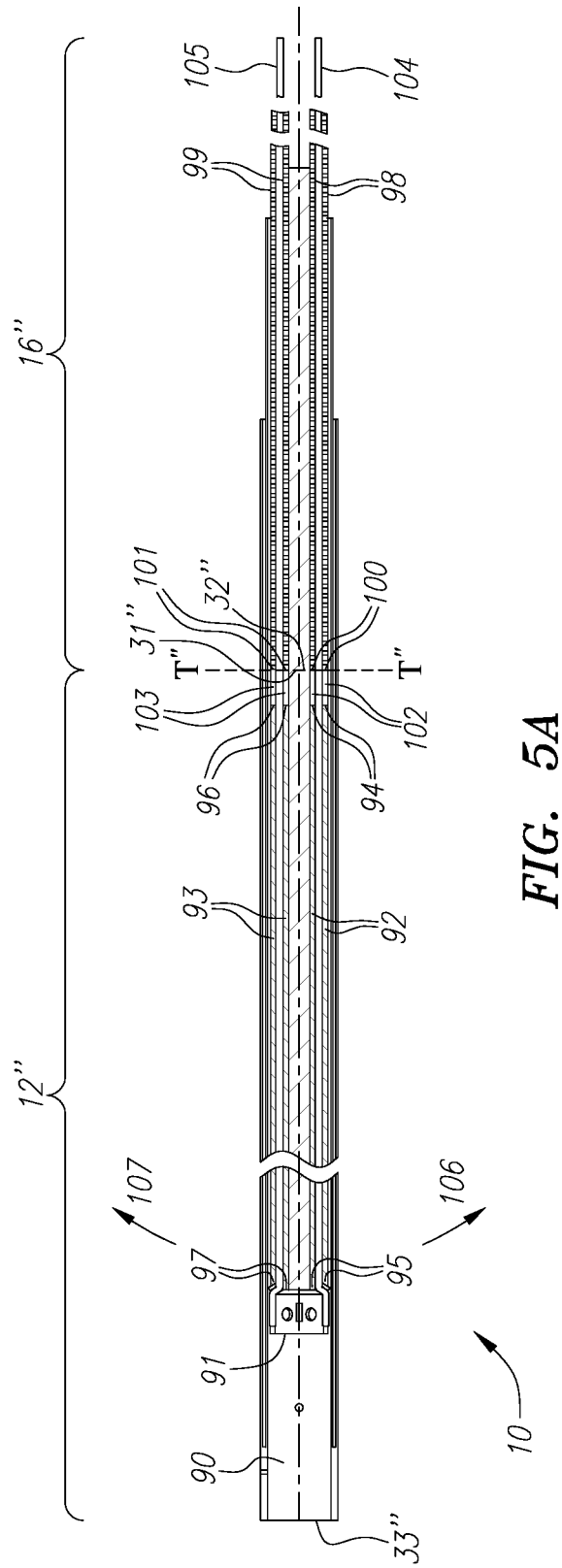
FIG. 5A illustrates an alternate embodiment of the embodiment seen in FIG. 2, in accordance with embodiments of the present disclosure.

FIG. 5A illustrates an alternate embodiment of the embodiment seen in FIG. 2, in accordance with embodiments of the present disclosure. The catheter 10 can include an elongated body that extends along a longitudinal axis. The elongated body can include a deflectable catheter shaft section 12" and a proximal catheter shaft section 16". In an example, the deflectable catheter shaft section 12" can include a distal end 33" and a proximal end 31". The proximal catheter shaft section 16" can include a distal end 32" and a proximal end (not shown). In some embodiments, the proximal end 31" of the deflectable catheter shaft section 12" can be approximately defined by transition line T"-T", for example, proximate to a distal ends 100, 101 of the compression coils 98, 99. In some embodiments, the distal end 32" of the proximal catheter shaft section 16" can be defined by the transition line T"-T", for example, proximate to the distal ends 98, 99, of the compression coils 98, 99.

In an example, the deflectable catheter shaft section 12" can include a pocket 90 that can be configured to accept tip assembly 15 and a pull ring 91. In some embodiments, the catheter 10 can include a lumen 85, which can include a first deflection lumen 87 and a second deflection lumen 88, as illustrated in FIG. 4. The first deflection lumen 87 and the second deflection lumen 88 can be diametrically opposed within the lumen 85 and can extend longitudinally through the proximal catheter shaft section 16" and the deflectable catheter shaft section 12".

In some embodiments, a first pull wire liner 92 and a second pull wire liner 93 can extend through a portion of each of the deflection lumens 87, 88, respectively, in the deflectable catheter shaft section 12". The first pull wire liner 92 can have a proximal end 94 and a distal end 95 and the second pull wire liner 93 can have a proximal end 96 and a distal end 97. The catheter 10 can include a first compression coil 98 and a second compression coil 99 that extend through a portion of each of the deflection lumens 87, 88 in the proximal shaft section 16". The first compression coil 98 can have a proximal end (not shown) and a distal end 100 and the second compression coil 99 can have a proximal end (not shown) and a distal end 101.

In some embodiments, a first gap 102 can be included between the proximal end 94 of the first pull wire liner 92 and a distal end 100 of the first compression coil 98 and a second gap 103 can be included between the proximal end 96 of the second pull wire liner 93 and the distal end 101 of the second compression coil 99. In some embodiments, a longitudinal length of the first gap 102 can be substantially equal to the longitudinal length of the second gap 103. A first pull wire 104 can extend through the first pull wire liner 92, the first gap 102, and the first compression coil 98, and a second pull wire 105 can extend through the second pull wire liner 93, the second gap 103, and the second compression coil 99.

In some embodiments, the deflectable catheter shaft section 12" can be configured to symmetrically deflect along a plane defined by the first and second pull wires 104, 105 and/or pull wire liners 92, 93. In an example, the pull wire liners 92, 93 can extend proximally along the deflectable catheter shaft section 12" substantially the same length, allowing for the deflectable catheter shaft section 12" to form similar and/or same curves as it is deflected in the direction of arrow 106 and deflected in the direction of arrow 107. As such, the deflectable catheter shaft section 12" can have a propensity to form curves with similar and/or the same curve angles when the deflectable catheter shaft section 12" is deflected in the direction of arrow 106 versus when it is deflected in the direction of arrow 107.

As discussed herein, embodiments of the present disclosure can eliminate the interference that occurs between the pull wire liner and compression coil and/or other components. As illustrated in FIG. 5A, embodiments of the present disclosure can include the first gap 102 between the first pull wire liner 92 and the first compression coil 98 and the second gap 103 between the second pull wire liner 93 and the second compression coil 99. As such, as the deflectable catheter shaft section 12" is deflected, the pull wire liners 92, 93 have space to move within the gaps, thus preventing interference between the pull wire liners 92, 93 and the compression coils 98, 99. This can provide a decreased deflection force and an increased curve angle associated with the deflectable catheter shaft section 12'.

Figure 5B:
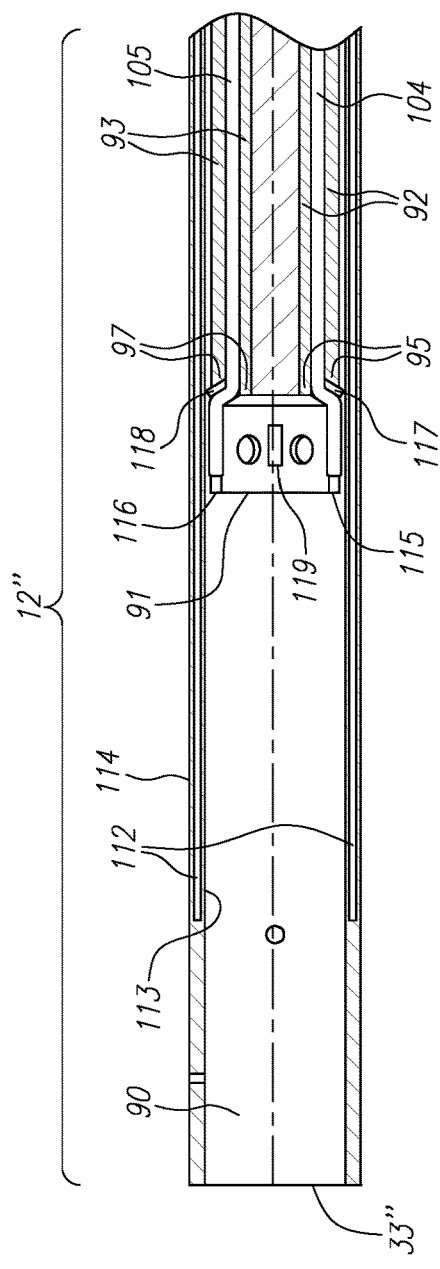
FIG. 5B illustrates a distal portion of the deflectable catheter shaft section seen in FIG. 5A, in accordance with embodiments of the present disclosure.

FIG. 5B illustrates a distal portion of the deflectable catheter shaft section seen in FIG. 5A, in accordance with embodiments of the present disclosure. The deflectable catheter shaft section 12" includes a distal end 33". In some embodiments, the catheter 10 can include a cylindrical braid structure(s) 112 placed around pull wire liners 92, 93, which can be disposed within diametrically-opposed lumens, as discussed herein. Deflectable catheter shaft section 12" can be constructed of a series of polymer layer(s) (e.g., inner polymer layer 113 and outer polymer layer 114) and braid structure(s) 112. In particular, one or more wires wound to form the cylindrical braid structure(s) 112 can substantially surround the pull wire liners 92, 93 through which the pull wires 104, 105 pass. In addition, a polymeric material, such as polyurethane, nylon, or various types of plastic materials such as polyether block amides offered under the trademark PEBAX®, which is a registered trademark of Arkema France, Puteaux, France, or any other suitable material, can also substantially surround the pull wire liners 92, 93.

The deflectable catheter shaft section 12" can include a pocket 90 that is configured to house a pull ring 91. The pull ring 91 can be attached within the pocket 90 via an adhesive 119, in some embodiments. The pull wire liners 92, 93 can be disposed over the pull wires 104, 105. A distal end 95, 97 of the pull wire liners 92, 93 can be attached to the pull ring 91 via an adhesive 117, 118. In addition, the distal end 115, 116 of the pull wires 104, 105 can be attached to the pull ring 91 via an adhesive.

Figure 5C:
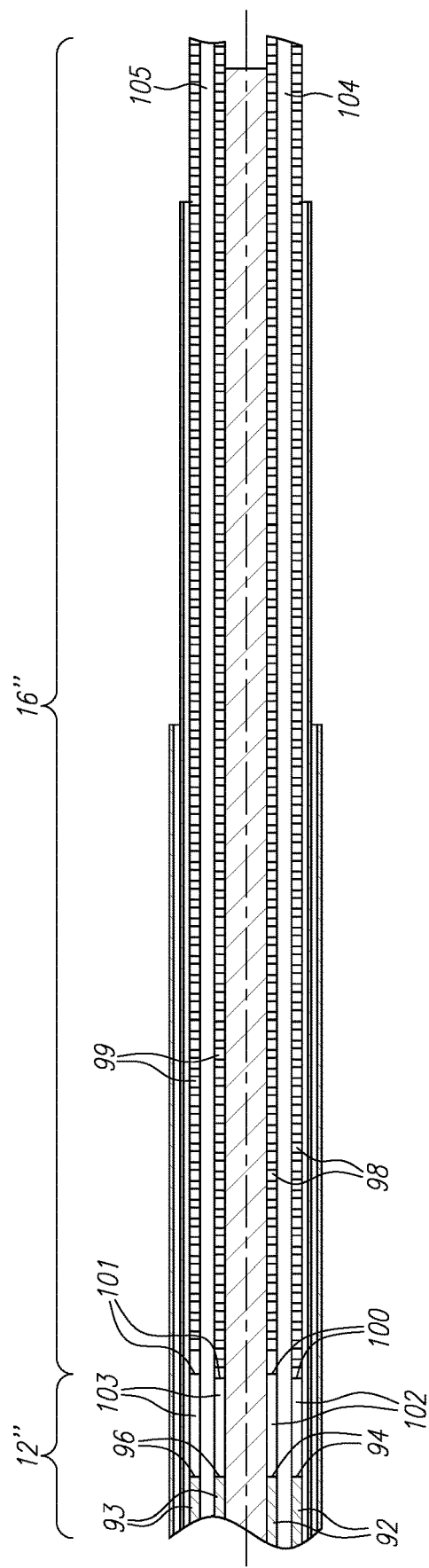
FIG. 5C illustrates a proximal portion of the deflectable catheter shaft section and a proximal portion of the catheter shaft seen in FIG. 5A, in accordance with embodiments of the present disclosure.

FIG. 5C illustrates a proximal portion of the deflectable catheter shaft section and a proximal portion of the catheter shaft seen in FIG. 5A, in accordance with embodiments of the present disclosure. The deflectable catheter shaft section 12" can include the first gap 102 between the proximal end 94 of the first pull wire liner 92 and the distal end 100 of the first compression coil 98 that can extend through a portion of the proximal shaft section 16". In addition, the deflectable catheter shaft section 12" can include the second gap 103 between the proximal end 96 of the second pull wire liner 93 and the distal end 101 of the second compression coil 99 that can extend through a portion of the proximal shaft section 16".

The first pull wire 104 can pass through the first compression coil 98, the first gap 102, and the first pull wire liner 92. The second pull wire 105 can pass through the second compression coil 99, the second gap 103, and the second pull wire liner 93. As discussed herein, the gaps 102, 103 can provide the pull wire liners 92, 93 space to move within the gaps 102, 103, as the deflectable catheter shaft section 12" is deflected. This can provide a decreased deflection force and an increased curve angle associated with the deflectable catheter shaft section 12". Also, the deflectable catheter shaft section 12" can be configured to symmetrically deflect along a plane defined by the first and second pull wires 104, 105 and/or pull wire liners 92, 93. In an example, the pull wire liners 92, 93 can extend proximally along the deflectable catheter shaft section 12" from the pull ring 91 substantially the same length, allowing for the deflectable catheter shaft section 12" to form similar and/or the same curves as it is deflected in the direction of arrow 106 and deflected in the direction of arrow 107 (shown in FIG. 5A). As such, the deflectable catheter shaft section 12" can have a propensity to form curves with the same and/or similar curve angles when it is deflected in the direction of arrow 106 and in the direction of arrow 107.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a deflectable catheter shaft section has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A deflectable catheter shaft section comprising the following:
   an elongated body extending along a longitudinal axis and comprising a distal end and a proximal end;
   first and second pull wires, wherein each of the first and second pull wires has a proximal end and a distal end, and wherein each of the first and second pull wires extends along the elongated body;
   first and second pull wire liners each disposed over a portion of one of the first and second pull wires, respectively, wherein each of the first and second pull wire liners has a proximal end and a distal end; and
   a first gap between the proximal end of the first pull wire liner and the proximal end of the elongated body and a second gap between the proximal end of the second pull wire liner and the proximal end of the elongated body, wherein a longitudinal length of the first gap is greater than a longitudinal length of the second gap.

2. The deflectable catheter shall section of claim 1, wherein:
   the first gap is an annular lumen that surrounds the first pull wire between the proximal end of the first pull wire liner and the proximal end of the elongated body; and
   the second gap is an annular lumen that surrounds the second pull wire between the proximal end of the second pull wire liner and the proximal end of the elongated body.

3. The deflectable catheter shaft section of claim 1, wherein the first and second pull wire liners are diametrically-opposed.

4. The deflectable catheter shaft section of claim 1, wherein:
   a bendable stiffening member is disposed over the first pull wire along a portion of the first gap; and
   the bendable stiffening member has a proximal end and a distal end.

5. The deflectable catheter shaft section of claim 4, wherein the distal end of the bendable stiffening member is spaced apart from the proximal end of the first pull wire liner and the proximal end of the bendable stiffening member is spaced apart from the proximal end of the elongated body.

6. The deflectable catheter shaft section of claim 1, further comprising a pocket at the distal end of the elongated body configured for attachment of a pull ring and tip assembly, wherein the pocket is defined by a recessed area in the distal end of the elongate body.

7. The deflectable catheter shaft section of claim 6, wherein a distal end of each of the first and second pull wires is connected to a pull ring disposed in the pocket at the distal end of the elongated body.

8. The deflectable catheter shaft section of claim 1, wherein an inner diameter of the pull wire liner is in a range of 0.0105 inches to 0.0120 inches and an outer diameter of the pull wire liner is in a range of 0.0140 inches to 0.0180 inches.

9. A catheter comprising the following:
   an elongated body extending along a longitudinal axis, the elongated body comprising a proximal catheter shaft section and a distal, deflectable catheter shaft section;
   first and second pull wires, wherein each of the first and second pull wires extends along the proximal catheter shaft section and along the deflectable catheter shaft section;
   first and second compression coils each disposed over one of the first and second pull wires, respectively, along the proximal catheter shaft section, wherein each of the first and second compression coils has a proximal end and a distal end; and
   first and second pull wire liners each disposed over a portion of one of the first and second pull wires, respectively, wherein each of the first and second pull wires has a proximal end and a distal end;
   a first gap between the proximal end of the first pull wire liner and the distal end of the first compression coil and a second gap between the proximal end of the second pull wire liner and the distal end of the second compression coil;
   a bendable stiffening member disposed along a portion of the first gap;
   a distal gap between the proximal end of the first pull wire liner and a distal end of the bendable stiffening member; and
   a proximal gap between the proximal end of the bendable stiffening member and the distal end of the first compression coil.

10. The catheter of claim 9, wherein a longitudinal length of the first gap is greater than a longitudinal length of the second gap.

11. The catheter of claim 9, wherein:
    each of the first and second pull wires has a proximal end and a distal end; and
    the distal end of each of the first and second pull wires is connected to a pull ring that is attached within a pocket at the distal end of the elongated body.

12. The catheter of claim 9, wherein each of the first and second pull wire liners comprise polytetrafluoroethylene.

13. The catheter of claim 9, wherein the bendable stiffening member includes a spring pack disposed over the first pull wire.

14. The catheter of claim 9, wherein the deflectable catheter shaft section is configured to asymmetrically deflect along a plane defined by the first and second pull wires.

15. A catheter comprising the following:
    an elongated body extending along a longitudinal axis, the elongated body comprising a proximal catheter shaft section and a distal, deflectable catheter shaft section wherein a first and second diametrically-opposed deflection lumen each extend longitudinally through the proximal catheter shaft section and the deflectable catheter shaft section;

first and second pull wire liners that extend through a portion of each of the deflection lumens in the deflectable shaft section, wherein each of the first and second pull wire liners has a proximal end and a distal end;

first and second compression coils that extend through a portion of each of the deflection lumens in the proximal shaft section, wherein each of the first and second compression coils has a proximal end and a distal end;

a first gap between the proximal end of the first pull wire liner and the distal end of the first compression coil and a second gap between the proximal end of the second pull wire liner and the distal end of the second compression coil, wherein a longitudinal length of the first gap is greater than a longitudinal length of the second gap; and a first pull wire that extends through the first pull wire liner, the first gap, and the first compression coil, and a second pull wire that extends through the second pull wire liner, the second gap, and the second compression coil.

16. The catheter of claim 15, wherein the deflectable catheter shaft section is configured to symmetrically deflect along a plane defined by the first and second pull wires.

17. The catheter of claim 15, wherein a distal end of the first and second pull wires and the distal end of the first and second pull wire liners is connected to a pun ring.

18. The catheter of claim 15, wherein the elongate body comprises a cylindrical braid structure over the first and second diametrically-opposed lumens.

* * * * *